(12) United States Patent
Shechter

(10) Patent No.: US 8,721,514 B2
(45) Date of Patent: May 13, 2014

(54) ELECTROMAGNETIC POSE SENSING OF HDR BRACHYTHERAPY APPLICATOR

(75) Inventor: Guy Shechter, Briarcliff Manor, NY (US)

(73) Assignee: Koninklijke Philips N.V., Eindhoven (NL)

( * ) Notice: Subject to any disclaimer, the term of this patent is extended or adjusted under 35 U.S.C. 154(b) by 623 days.

(21) Appl. No.: 12/680,279

(22) PCT Filed: Oct. 20, 2008

(86) PCT No.: PCT/IB2008/054318
§ 371 (c)(1),
(2), (4) Date: Mar. 26, 2010

(87) PCT Pub. No.: WO2009/053897
PCT Pub. Date: Apr. 30, 2009

(65) Prior Publication Data
US 2010/0312038 A1 Dec. 9, 2010

Related U.S. Application Data

(60) Provisional application No. 60/982,820, filed on Oct. 26, 2007.

(51) Int. Cl.
*A61N 5/00* (2006.01)
(52) U.S. Cl.
USPC ............... 600/3; 600/414; 600/426; 600/424; 600/407; 356/247; 356/396; 128/897; 128/898
(58) Field of Classification Search
USPC .............. 600/3, 424, 407, 414, 426; 356/247, 356/396; 128/897, 898
See application file for complete search history.

(56) References Cited

U.S. PATENT DOCUMENTS

| 2005/0090733 A1* | 4/2005 | Van Der Lugt et al. ....... 600/411 |
| 2006/0094923 A1* | 5/2006 | Mate ................................ 600/3 |
| 2007/0043291 A1 | 2/2007 | Fidel et al. |
| 2007/0066880 A1* | 3/2007 | Lee et al. ...................... 600/407 |

FOREIGN PATENT DOCUMENTS

| EP | 1524011 | 4/2005 |
| WO | WO2006039698 | 4/2006 |
| WO | WO2007043943 | 4/2007 |

OTHER PUBLICATIONS

Y. Wantanabe et al., "A System for Nonradiographic Source Localization and Real-time Planning of Intraoperative High Dose Rate Brachytherapy", Medical Physics, AIP, Melville, NY, US, Dec. 1997, vol. 24, No. 12, pp. 2014-2023.

\* cited by examiner

*Primary Examiner* — Christine Matthews
*Assistant Examiner* — Sunita Reddy

(57) ABSTRACT

An implantable applicator (10) has at least one guide channel (12) for guiding a radioactive seed or source (66) to a target region. A plurality of imageable fiducials (40) are configured for attachment to the patient adjacent the target region. Electromagnetic sensors (18, 20, 22, 20', 42) are mounted to the applicator and the imageable fiducials. An electromagnetic tracking system determines the relative position of the applicator mounted sensors (18, 20, 22, 20') and the fiducial mounted sensors (42). A localizing processor (52) generates a map of the sensors which is combined (56) with a high resolution image (46). A comparing processor (70) monitors for changes in sensor positions, generates a movement correction transform (72) which transforms (74) the planning image into a transformed planning image (76). A brachytherapy treatment processor (60) generates a treatment plan (60a) from the planning image or the transformed planning image for controlling an auto-loader (64) which moves the radioactive source or seed (66) through the channels (12) of the applicator (10).

23 Claims, 2 Drawing Sheets

ELECTROMAGNETIC POSE SENSING OF HDR BRACHYTHERAPY APPLICATOR

The present application relates to the therapeutic arts. It finds particular application in conjunction with high dose rate (HDR) brachytherapy and will be described with particular reference thereto. However, it is to be appreciated that the invention will also find application in conjunction with other therapeutic treatments, such as low dose brachytherapy, positioning other treatment sources, and the like.

Cancer is often treated with a combination of therapies, such as surgery, chemotherapy, radiation therapy, and the like. For example, a tumor is often removed surgically, after which the patient is treated with chemotherapy or radiation to kill any cancerous cells which were not removed. In one radiation treatment, a beam of x-rays from a linear accelerator are directed through a target region(s). By contrast, in brachytherapy, a seed(s) is inserted into a target region to irradiate the target region from within.

In HDR brachytherapy, an applicator in the form of a catheter is positioned in the patient, extending through the target area to be irradiated. A high dose rate source, e.g., an iridium 192 pellet or seed is moved through the catheter on the end of a wire and dwells at one or more preplanned positions for a planned period of time. This treatment is repeated, typically, once or twice per day over a period of several days.

In the example of treating breast cancer, following a lumpectomy, an applicator is surgically implanted into the target region to be irradiated. A suitable applicator is a Cianna SAVI™ HDR applicator available from Cianna Medical of Aliso Veijo, Calif. A CT scan is conducted to generate a high resolution image of the applicator and tissue in the target region. This image is used for a brachytherapy planning session to plan where along the applicator the seed will be positioned and for how long. The planned brachytherapy treatment is then applied once or twice a day for several days. Particularly with soft tissue such as the breast, there is the possibility that the applicator can shift relative to the treated tissue. To assure that the applicator is in the proper position, hence that the planned treatment is being delivered, a CT scan is conducted prior to each brachytheraphy session.

The present application describes a new and improved apparatus and method which overcomes these problems and others.

In accordance with one aspect, a brachytherapy apparatus is provided. An implantable applicator provides at least one guide channel for guiding a radioactive source or seed to a target region. A plurality of electromagnetic sensors are mounted on the applicator. A plurality of imageable fiducials which include electromagnetic sensors are configured for attachment to a patient adjacent the target area. An electromagnetic tracking system determines the relative position of the applicator mounted sensors and the fiducial sensors.

In accordance with another aspect, a brachytherapy method is provided. An applicator having at least one radiation source or seed receiving channel and a plurality of electromagnetic sensors is implanted in soft tissue adjacent a target area to be irradiated. The imageable fiducials which contain electromagnetic sensors are mounted to the soft tissue adjacent the target region. A high resolution planning image of the target region including the applicator and the fiducials is generated. The position of the applicator mounted sensors relative to the fiducial mounted sensors is electromagnetically tracked.

One advantage resides in a reduction of radiation exposure. Another advantage resides in assured accuracy of a planned brachytherapy.

Still further advantages and benefits will become apparent to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

Figure 1:
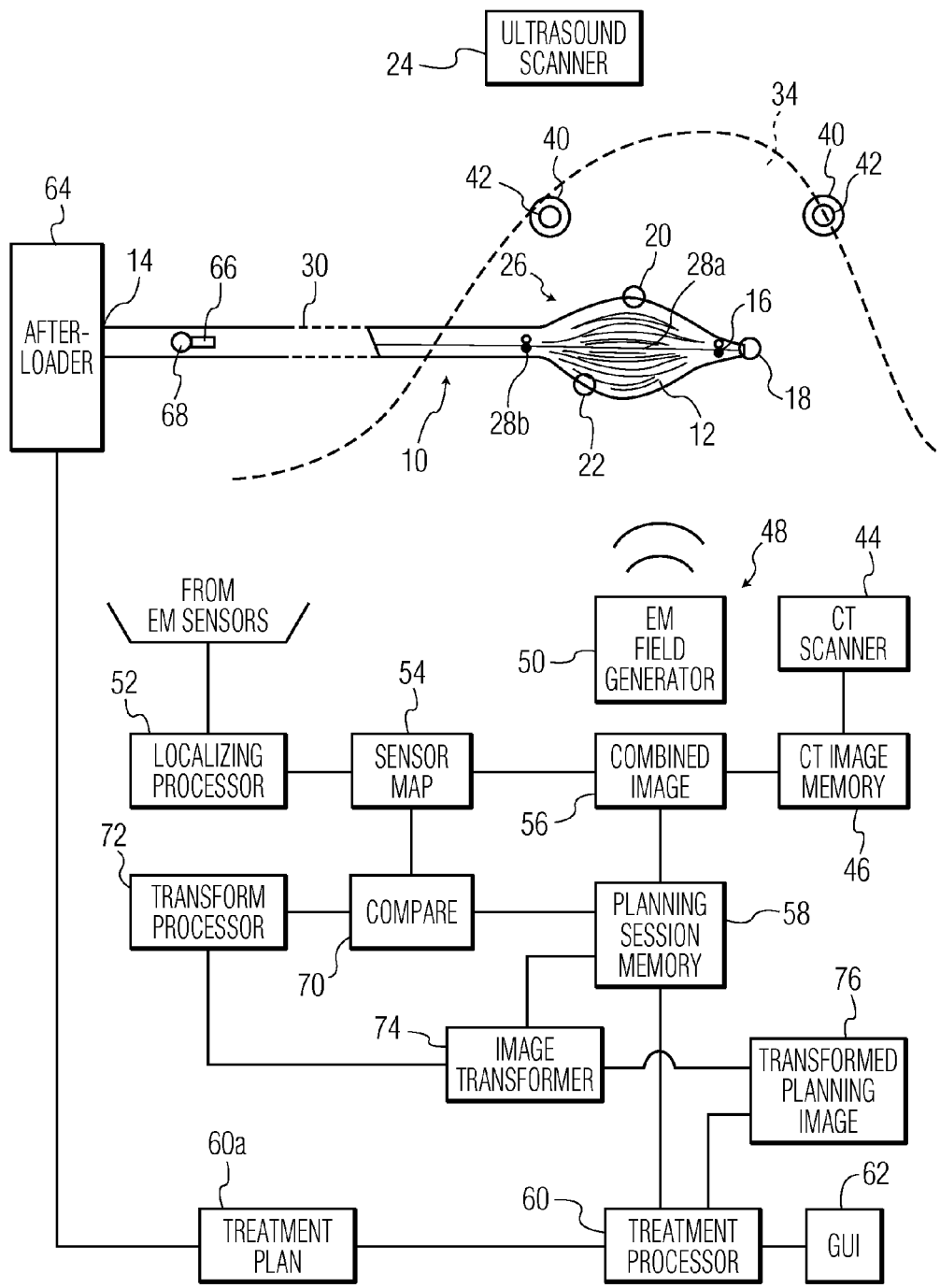
FIG. 1 is a diagrammatic illustration of a brachytherapy system including an instrumented applicator.

With reference to FIG. 1, a multi-catheter applicator 10 includes a plurality of guide channels or cannulae 12 which extend from a radioactive seed receiving end 14 to a tip 16 at an opposite implanted end. A first electromagnetic sensor 18 is disposed on the tip 16 of the applicator. At least one additional electromagnetic sensor 20 is mounted on or in one of the cannulae. Optionally, one or more additional electromagnetic sensors 22 are provided on other cannulae.

In one method of use, lumpectomy surgery is performed to remove a cancerous or potentially cancerous lump. After the surgery, the applicator 10 is inserted in a collapsed position. That is, all of the cannulae extend parallel to each other and closely adjacent in a bunch of minimal cross-section. The applicator is positioned using an ultrasonic guidance system 24 to place the applicator in the selected position, typically with a head portion 26 within the volume vacated by the lump. An expansion mechanism, such as a draw rod 28a is operated to expand the inserted head portion 26 of the applicator, e.g., to bring the tip 16 and a ring 28b towards each other, causing the sections of the cannulae in a head portion 26 to expand relative to a shaft portion 30. The cannulae sections of the head portion are expanded to an appropriate bulbous configuration to bring the seed delivery paths defined by the cannulae adjacent tissue 34 to be irradiated.

After insertion of the cannulae, a plurality of fiducials 40, e.g., three fiducials or more, are mounted on the patient adjacent the inserted head portion 26 of the applicator 10 and the tissue 34. Each fiducial includes an electromagnetic sensor unit 42 and is imageable by a high resolution imaging modality, such as a CT scanner 44. A high resolution image of the target region including the applicator 10 and the surrounding tissue is generated by the CT scanner 44 and stored in a CT image memory 46.

An electromagnetic position system 48 performs an electromagnetic positioning operation. That is, electromagnetic signals are generated by a field generator 50 which sends out electromagnetic signals that are received by the electromagnetic sensors 18, 20, 22, which are mounted on the applicator and the sensors 42 which are mounted to the patient. A localizing processor 52 determines the relative locations of the applicator mounted sensors 18, 20, 22 relative to the patient mounted sensors 42 and generates a sensor map 54. Because the fiducials 40 are also imaged in the CT image, the positions of the electromagnetic sensors 18, 20, 22 on the applicator relative to the fiducial mounted sensors 42 are also known in the coordinate system of the CT scanner and the CT image 46 which it generates.

In one embodiment, the positions or locations of the electromagnetic sensors on the applicator from the sensor map 54 are superimposed onto the CT image 46 to generate a combined image 56 stored in a planning session memory 58. In another embodiment, the applicator mounted sensors are imageable by the CT scanner and, thus, appear in the CT image 46.

The combined image 56 is utilized in a brachytheraphy planning session to plan the brachytherapy. This planning session typically involves planning in which catheters a radioactive seed will be placed, where in each catheter, and how long the seed will dwell in each location in each catheter. Each radioactive seed will generate a known dose per unit time in each of a plurality of concentric generally-spherical or ovoid regions surrounding the seed. By positioning the seed in different locations, for different periods of time, the total radiation dose in regions of the surrounding tissue can be determined. In the planning session, the desired dose to be delivered in each of one or more designated surrounding tissue regions is determined by the treating oncologist and the positions and duration of the seed(s) are calculated in order to match the delivered dose distribution to the desired dose distribution. The calculations are advantageously performed by a treatment processor 60 which is suitably programmed to generate a treatment plan 60a and optimizes the positioning of seeds to achieve the oncologist's selected dose distribution input on a graphic user interface 62.

An afterloader 64 is programmed with the planned therapy session, loaded with the appropriate radioactive seed(s) 66 and attached to a loading end of the stem 30 of the applicator. In one embodiment, each seed 66 carries an electromagnetic sensor 68. Thereafter, the afterloader moves the seed through each of the selected catheters to each of the calculated locations for each of the calculated durations.

Again, brachytheraphy sessions are typically administered one, two, or a few times a day for several days, e.g., 1-2 weeks. Between brachytheraphy sessions, the applicator remains implanted. An alignment confirmation/readjustment procedure is performed prior to each brachytherapy session. When the next brachytheraphy session is to commence, the electromagnetic localizer system 48 is used to localize or determine the position and orientation of the applicator. Specifically, the field generator 50 generates electromagnetic fields which are sensed by the sensors 18, 20, 22 on the applicator and sensors 42 on the patient. The relative locations of the applicator sensors and the patient mounted sensors on the combined image 56 stored in the planning image memory 58 are compared by a comparing processor or algorithm 70 with the current relative locations of the applicator mounted electromagnetic sensors 18, 20, 22 and the patient mounted electromagnetic sensors 42 in the sensor map 54. If the relative positions have not changed indicating that the applicator has not changed orientation or location relative to the soft tissue, the afterloader 64 is reconnected and the next brachytherapy session is commenced.

However, if a comparing processor 70 determines that the positions have changed, one option is to attempt to reposition the applicator as additional measurements of the electromagnetic sensor locations are taken, trying to bring the applicator back or as close as possible to its original position and orientation. If the applicator is not in the original position at which the therapy was planned, a transform . is determined by a transform processor 72 between the current and original location of the applicator relative to the tissue mounted electromagnetic sensors, hence the surrounding tissue and the target area. This transform is used by an image transforming processor 74 to operate on the combined image 56 from the planning image memory 58 to shift the relative location of the applicator and the target region in accordance with the transform to form a transformed therapy planning image 76. This shifted information is fed to the automatic therapy planning processor 60 to generate anew brachytherapy plan 60a. The new brachytherapy plan is loaded into the afterloader 64 and the next brachytherapy session is commenced.

In another alternate embodiment, the electromagnetic sensor 68 attached to the radioactive source or seed 66 is used to determine the current position of the seed. This assures that the brachytherapy plan is being followed. The treatment planning processor 60 can adjust the treatment plan or the positioning of the radiation seed or the applicator, as necessary, on the fly.

In one brachytherapy adapting planning embodiment, the applicator is implanted, a diagnostic image is generated, and a dose plan is created. During the dose delivery, the applicator and/or the seed are tracked and a delivered dose is computed. For example, the target tissue could be divided into a 3D matrix of subregions. By mapping the EM tracked seed location into the 3D matrix, the cumulative dose in each subregion can be continuously or intermittently updated or incremented based on time and distance from the source. The delivered dose can be monitored by computer and/or clinician. If a deviation from the dose plan is detected, an updated dose plan is generated.

In another embodiment, the position of the applicator is monitored as the dose plan is administered. If the applicator moves such that the seed is not in the planned location or if the cannulae of the applicator cannot deliver the seed to the remaining planned positions, the dose plan is recalculated.

The electromagnetic tracking can be performed not only prior to each therapy session, but can also be performed during each brachytherapy session. Performing the electromagnetic tracking during a brachytheraphy session assures that there is no motion of the applicator during the session and, if any motion occurs, the treatment planning calculator recalculates the brachytherapy plan on the fly.

Tracking the radioactive source or seed directly and comparing its position to the applicator and patient mounting sensors monitors the therapy delivery and validates that the dose is being delivered in the right place. In addition to modifying the dose plan intra-procedurally, this feedback can also be used to create a record of the treatment plan or a radiation map showing the radiation actually delivered in each session.

Various types of applicators are contemplated. For example, with reference to FIG. 2, the applicator can have a single guide channel or cannula 12 which extends from the loading end 14 to the tip 16. An expandable balloon 32 is disposed around the head portion 26 to be selectively expanded firmly against the surrounding tissue. An electromagnetic sensor 18 is mounted on the up 16 and another electromagnetic sensor 20' is mounted on the cannula adjacent the opposite end of the balloon 32. Because the radioactive seed is only positionable along the one-dimensional trajectory defined by the guide channel or cannula 12, two electromagnetic sensors are sufficient to determine the location of the catheter in three dimensions relative to the surrounding tissue. Optionally, additional sensors can be positioned on the balloon 32.

Figure 2:
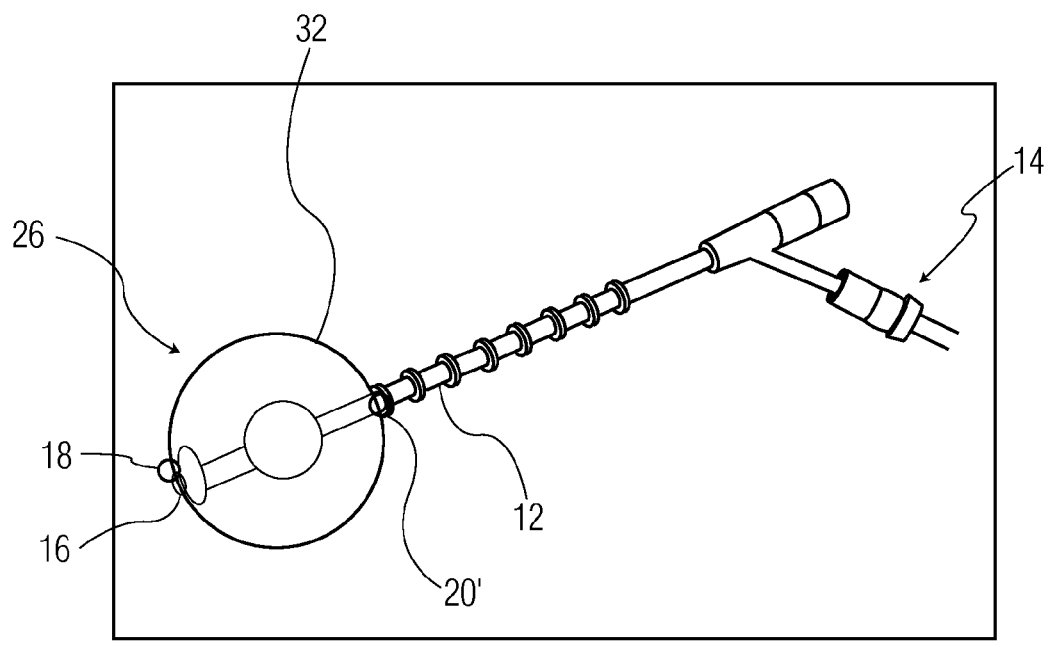
FIG. 2 illustrates an alternate embodiment of an instrumented applicator.
Figure 3:
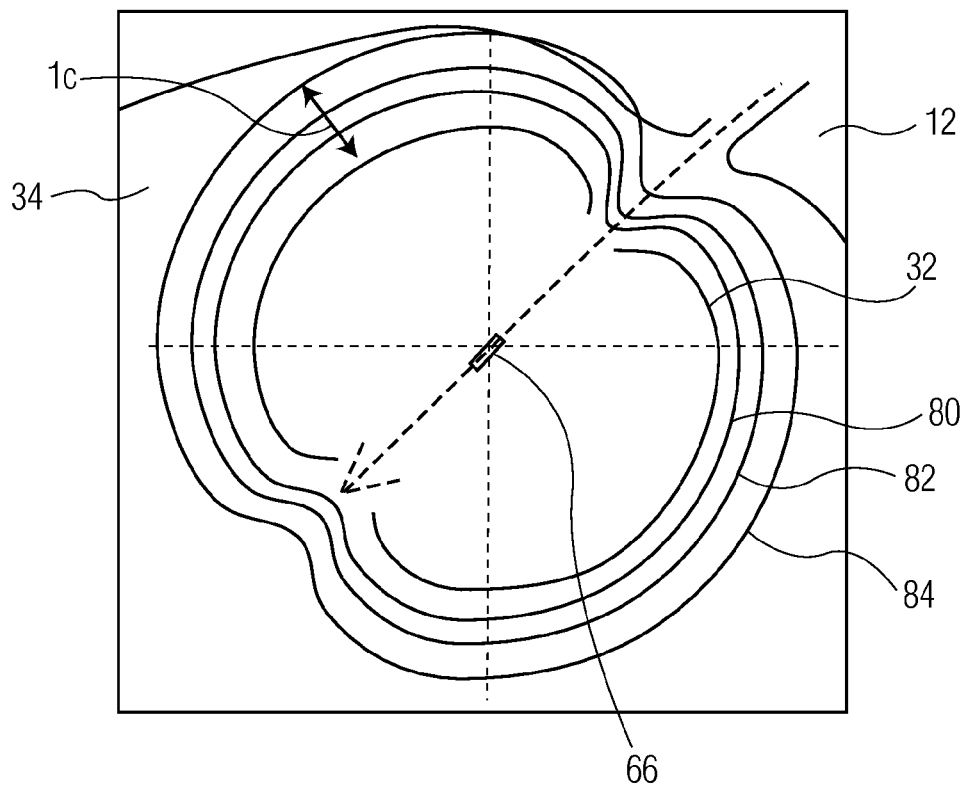
FIG. 3 depicts a CT image of an implanted brachytherapy applicator.

FIG. 3 depicts an exemplary CT scan of the applicator of FIG. 2 implanted in soft tissue 34. When the seed 66 is placed at a center of the balloon 32, the dose in surrounding regions can be determined. In the example of FIG. 2, the region denoted by 80 receives a dose of 5.1 Gy, the surrounding region 82 receives a dose of 4.25 Gy, and the outer region 84 receives a dose of 3.4 Gy.

Various types of electromagnetic locator systems can be utilized. In one example, the field generator has a plurality of antennas at different orientations. The sensors pick up the signals from the antennas at the various orientations. From their relative signal characteristics, e.g., relative signal strength, relative phase, etc., the location of the sensor relative to the antennas is determined. In another embodiment, the sensors have receiving coils or antennas with different orientations. In one embodiment, the sensors are connected with the localizer processor 52 by wires running down the stem 30 of the applicator. In another embodiment, a wireless communication path is used.

Other types of applicators and other types of tracking systems are also contemplated.

Although described with reference to the breast, other brachytherapy treatments are also contemplated such as prostate, head and neck, and gynecological.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A brachytherapy apparatus, comprising:
an implantable applicator which provides at least one guide channel for guiding a radioactive source or seed to a target region; a plurality of electromagnetic sensors mounted to the applicator;
a plurality of imageable fiducials which include fiducial electromagnetic sensors, the fiducials being configured for attachment to a patient adjacent the target region;
an electromagnetic tracking system that determines a relative position of the electromagnetic sensors and the fiducial electromagnetic sensors; and
a treatment processor that plans a brachytherapy treatment session at least partially based on a combination of the relative position of the electromagnetic sensors and the fiducial electromagnetic sensors and on a planning image including at least the implantable applicator implanted within the patient adjacent the target region and the imageable fiducials attached to the patient adjacent the target region.

2. The apparatus according to claim 1, further including: a comparing processor that determines if and in what manner the electromagnetic sensors have moved relative to the fiducial electromagnetic sensors.

3. The apparatus according to claim 1, wherein the planning of the brachytherapy treatment session by the treatment processor includes a calculation of a brachytherapy treatment plan including a positioning, movement, and timing for moving the radioactive source or seed through the at least one guide channel of the applicator.

4. The apparatus according to claim 3, further including: a comparing processor that determines relative location of the electromagnetic sensors and the fiducial electromagnetic sensors.

5. The apparatus according to claim 4, further including: a transform processor that determines how the applicator has moved relative to a surrounding tissue, the determination of applicator motion being conveyed to the treatment processor for recalculating the brachytherapy treatment plan in accordance with the determined movement.

6. The apparatus according to claim 3, further including: an afterloader connected with the applicator for moving the radioactive source or seed through the at least one guide channel in accordance with the calculated brachytherapy treatment plan.

7. The apparatus according to claim 3, wherein the electromagnetic tracking system determines a map of the electromagnetic sensors and the fiducial electromagnetic sensors during the brachytherapy treatment session implementing the brachytherapy treatment plan, and wherein the treatment processor adjusts the brachytherapy treatment plan during the brachytherapy treatment session.

8. The apparatus according to claim 7, wherein a cumulative dose to subregions of the target region is determined during the implementation of the brachytherapy treatment plan, and wherein in response to at least one of (1) the cumulative dose in the subregions deviating from the brachytherapy treatment plan or (2) sensing movement of the radioactive source or seed or the applicator, the treatment processor recalculates the brachytherapy treatment plan.

9. The apparatus according to claim 7, further including:
a sensor connected to the radioactive source or seed.

10. The apparatus according to claim 3, further including:
a planning image memory that stores the planning image as generated from a high resolution imaging system, the planning image including the implantable applicator, tissue in the target region, and the imageable fiducials.

11. The apparatus according to claim 10, further including:
an image combining processor that superimposes a map of the electromagnetic sensors on the planning image.

12. The apparatus according to claim 11, further including:
at least one processor that determines relative motion between the applicator and the fiducials and that generates a corrective transform; and an image transform processor that transforms at least a portion of the planning image in accordance with the corrective transform.

13. The apparatus according to claim 10, wherein the applicator includes a plurality of the guide channels.

14. The apparatus according to claim 13, further including:
an afterloader that moves the radioactive source or seed among the plurality of guide channels; and
wherein the treatment processor further plans the brachytherapy treatment session based on a desired radiation dose input by an oncologist, the treatment processor conveying appropriate electronic instructions to the afterloader.

15. A brachytherapy method, comprising: implanting an applicator having at least one guide channel and a plurality of electromagnetic sensors affixed thereto in soft tissue adjacent a target region to be irradiated; positioning imageable fiducials which contain fiducial electromagnetic sensors relative to the soft tissue adjacent the target region; generating a planning image of the target region including at least the applicator implanted in the soft tissue adjacent the target region and the imageable fiducials positioned relative to the soft tissue adjacent the target region; electromagnetically tracking the position of the electromagnetic sensors relative to the fiducial electromagnetic sensors; and planning a brachytherapy treatment session at least partially based on a combination of the planning image and of the relative position of the electromagnetic sensors and the fiducial electromagnetic sensors.

16. The method according to claim 15, wherein the brachytherapy treatment session includes brachytherapy indicating a position and a duration of at least one radioactive source or seed within the at least one guide channel.

17. The method according to claim 16, further including:
electromagnetically tracking a position and orientation of the applicator during the planned brachytherapy treatment session; and dynamically adjusting the planned brachytherapy treatment session in accordance with a change in the tracked position and orientation of the applicator.

18. The method according to claim 17, further including: performing the brachytherapy treatment session using the at least one radioactive source or seed to which an additional electromagnetic sensor has been affixed; during the brachytherapy treatment session, electromagnetically monitoring a location of each radioactive source or seed; and dynamically adjusting the brachytherapy treatment session in accordance with the determined position of the radioactive source or seed.

19. The method according to claim 15, further including: monitoring the relative position of the electromagnetic sensors relative to the fiducial electromagnetic sensors prior to each of a plurality of brachytherapy treatment sessions.

20. The method according to claim 15, further including: calculating a cumulative radiation dose planned to be delivered to each of a plurality of subregions of the target region during the brachytherapy treatment session; during the brachytherapy treatment session, calculating the cumulative dose delivered to each of the subregions; in response to either (1) the delivered cumulative dose deviating from the planned cumulative dose or (2) sensing movement of the seed or the applicator from a planned position, re-planning a remainder of the brachytherapy treatment session.

21. The method according to claim 15, further including: performing the brachytherapy treatment session using at least one radioactive source or seed in combination with an additional electromagnetic sensor; during the brachytherapy treatment session, electromagnetically monitoring a location of each radioactive source or seed; and dynamically adjusting the planned brachytherapy treatment session in accordance with the position of the radioactive source or seed.

22. A non-transitory computer-readable medium carrying a computer program which controls a computer to perform the steps of:

implanting an applicator having at least one guide channel and a plurality of electromagnetic sensors affixed thereto in soft tissue adjacent a target region to be irradiated;

positioning imageable fiducials which contain fiducial electromagnetic sensors relative to the soft tissue adjacent the target region;

generating a planning image of the target region including at least the applicator implanted in the soft tissue adjacent the target region and the imageable fiducials positioned relative to the soft tissue adjacent the target region;

electromagnetically tracking a position of the electromagnetic sensors relative to the fiducial electromagnetic sensors; and planning a brachytherapy treatment session at least partially based on a combination of the planning image and of the relative position of the electromagnetic sensors and the fiducial electromagnetic sensors.

23. A brachytherapy system, comprising: means for generating a planning image of a target region to be irradiated, the planning image including at least an applicator and imageable fiducials, wherein the applicator has at least one guide channel and a plurality of electromagnetic sensors affixed thereto and is adapted to be implanted in soft tissue adjacent the target region, and wherein the fiducials contain fiducial electromagnetic sensors and are adapted to be positioned relative to the soft tissue adjacent the target region;

means for electromagnetically tracking a position of the electromagnetic sensors relative to the fiducial electromagnetic sensors; and means for planning a brachytherapy treatment session at least partially based on a combination of the planning image and of the relative position of the electromagnetic sensors and the fiducial electromagnetic sensors.

* * * * *